US012714862B2

(12) United States Patent
Asp et al.

(10) Patent No.: US 12,714,862 B2
(45) Date of Patent: Aug. 25, 2026

(54) BIDIRECTIONAL SPIKE-TIMING-DEPENDENT BRAIN NETWORK GAIN CONTROL

(71) Applicant: Mayo Foundation for Medical Education and Research, Rochester, MN (US)

(72) Inventors: Anders J. Asp, Rochester, MN (US); Jose L. Lujan, Byron, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 204 days.

(21) Appl. No.: 18/787,224

(22) Filed: Jul. 29, 2024

(65) Prior Publication Data

US 2024/0382762 A1 Nov. 21, 2024

Related U.S. Application Data

(62) Division of application No. 17/394,366, filed on Aug. 4, 2021, now Pat. No. 12,076,568.

(60) Provisional application No. 63/067,134, filed on Aug. 18, 2020.

(51) Int. Cl.
*A61N 1/36* (2006.01)
*A61N 1/05* (2006.01)

(52) U.S. Cl.
CPC ....... *A61N 1/36192* (2013.01); *A61N 1/0529* (2013.01); *A61N 1/36125* (2013.01); *A61N 1/36167* (2013.01)

(58) Field of Classification Search
None
See application file for complete search history.

(56) References Cited

U.S. PATENT DOCUMENTS

| | | | |
|---|---|---|---|
| 8,000,794 B2 | 8/2011 | Lozano | |
| 10,039,930 B2 | 8/2018 | Vallejo et al. | |
| 11,040,197 B2 | 6/2021 | Ludwig et al. | |
| 12,076,568 B2 | 9/2024 | Asp et al. | |
| 2009/0105786 A1 | 4/2009 | Fetz et al. | |
| 2012/0265262 A1* | 10/2012 | Osorio | A61N 1/36114 607/45 |
| 2016/0256689 A1 | 9/2016 | Vallejo et al. | |
| 2016/0271392 A1 | 9/2016 | Vallejo et al. | |
| 2016/0271413 A1 | 9/2016 | Vallejo et al. | |
| 2017/0106203 A1* | 4/2017 | Schneider | A61N 2/006 |
| 2017/0120043 A1 | 5/2017 | John | |

(Continued)

OTHER PUBLICATIONS

Albin et al., "The functional anatomy of basal ganglia disorders," Trends Neurosciences, 1989, 12(10):366-375.

(Continued)

*Primary Examiner* — Michael W Kahelin
(74) *Attorney, Agent, or Firm* — Fish & Richardson P.C.

(57) ABSTRACT

In an example method for increasing synaptic gain in a region of a brain of a subject, a first electromagnetic pulse is applied to a first neural element of a first neuron of the subject using a first electrode. The first neural element includes a first synapse coupled to a second neuron of the subject. Subsequent to applying the first electromagnetic pulse to the first neural element, a second electromagnetic pulse is applied to a second neural element of the second neuron using a second electrode.

13 Claims, 13 Drawing Sheets

(56) References Cited

U.S. PATENT DOCUMENTS

| | | | |
|---|---|---|---|
| 2018/0028812 | A1 | 2/2018 | Vallejo et al. |
| 2018/0243562 | A1 | 8/2018 | Vallejo et al. |
| 2018/0243563 | A1 | 8/2018 | Vallejo et al. |
| 2018/0250513 | A1 | 9/2018 | Vallejo et al. |
| 2018/0353758 | A1 | 12/2018 | Vallejo et al. |
| 2022/0054844 | A1 | 2/2022 | Asp et al. |

OTHER PUBLICATIONS

Anderson et al., "Anodic stimulation misunderstood: preferential activation of fiber orientations with anodic waveforms in deep brain stimulation," J. Neural Engineering, Jan. 14, 2019, 16(1):016026.

Anderson et al., "Deep brain stimulation for treatment-resistant depression: Efficacy, safety and mechanisms of action," Neurosci. Biobehav. Reviews, Sep. 2012, 36(8):1920-1933.

Asp et al., "A Low-Cost Humidity Control System to Protect Microscopes in a Tropical Climate," Ann. Glob. Health, Feb. 13, 2020, 86(1):16.

Asp et al., "Deep brain stimulation re-imagined: An ultra-low frequency spike timing dependent plasticity-based approach for treating alcohol use disorder," preprint, Research Square, posted on Feb. 2022, 26 pages, doi: 10.21203/rs.3.rs-1328464/v1.

Asp et al., "Optogenetic self-stimulation of the infralimbic-accumbens pathway blunts the development of cocaine sensitization," Presented at Proceedings of the Society for Neuroscience 2014 Annual Meeting, Washington, D.C., USA, Nov. 15-19, 2014, 2 pages.

Asp et al., "Optogenetic self-stimulation of the infralimbic-accumbens pathway: Opposing effects of abstinence from repeated cocaine and cocaine re-exposure," Presented at Proceedings of the Minnesota Neuromodulation Symposium, Minneapolis, MN, USA, Apr. 14-15, 2016, MNS 191, 1 page.

Balleine et al., "The Role of the Dorsal Striatum in Reward and Decision-Making, " J. Neuroscience, Aug. 1, 2007, 27(31):8161-8165.

Becker, "Alcohol Dependence, Withdrawal, and Relapse," Alcohol Res. Health, 2008, 31(4):348-361.

Benabid et al., "Combined (thalamotomy and stimulation) stereotactic surgery of the VIM thalamic nucleus for bilateral Parkinson disease," Appl. Neurophysiology, 1987, 50(1-6):344-346.

Benneyworth et al., "Synaptic Depotentiation and mGluR5 Activity in the Nucleus Accumbens Drive Cocaine-Primed Reinstatement of Place Preference, " J. Neuroscience, Jun. 12, 2019, 39(24):4785-4796.

Bi et al., "Synaptic Modifications in Cultured Hippocampal Neurons: Dependence on Spike Timing, Synaptic Strength, and Postsynaptic Cell Type," J. Neuroscience, Dec. 16, 1998, 18(24):10464-10472.

Bittar et al., "Deep brain stimulation for pain relief: a meta-analysis," J. Clin. Neuroscience, Jun. 2005, 12(5):515-519.

Broen et al., "Impulse control and related disorders in Parkinson's disease patients treated with bilateral subthalamic nucleus stimulation: a review," Parkinsonism Relat. Disorders, Jul. 2011, 17(6):413-417.

Brzosko et al., "Neuromodulation of Spike-Timing-Dependent Plasticity: Past, Present, and Future," Neuron, Aug. 21, 2019, 103(4):563-581.

Calabresi et al., "Direct and indirect pathways of basal ganglia: a critical reappraisal," Nat. Neuroscience, Jul. 28, 2014, 17(8):1022-1030.

Calipari et al., "In vivo imaging identifies temporal signature of D1 and D2 medium spiny neurons in cocaine reward," Proc. Natl. Acad. Sci. USA, Mar. 8, 2016, 113(10):2726-2731.

Cheng et al., "Distinct Synaptic Strengthening of the Striatal Direct and Indirect Pathways Drives Alcohol Consumption," Biol. Psychiatry, Jun. 2017, 81(11):918-929.

Cheng et al., "The use of chemogenetic approaches in alcohol use disorder research and treatment," Alcohol, Feb. 2019, 74:39-45.

Corbit et al., "Habitual Alcohol Seeking: Time Course and the Contribution of Subregions of the Dorsal Striatum," Biol. Psychiatry, Sep. 2012, 72(5):389-395.

Creed et al., "Refining deep brain stimulation to emulate optogenetic treatment of synaptic pathology," Science, Feb. 6, 2015, 347(6222):659-664.

Creed, "Current and emerging neuromodulation therapies for addiction: insight from pre-clinical studies," Curr. Opin. Neurobiology, Apr. 2018, 49:168-174.

Cui et al., "Endocannabinoid dynamics gate spike-timing dependent depression and potentiation," eLife, Feb. 27, 2016, 5:e13185, 32 pages.

D'Souza et al., "Chronic D1 agonist and ethanol coadministration facilitate ethanol- mediated behaviors," Pharmacol. Biochem. Behavior, Sep. 2003, 76(2):335-342.

Deniau et al., "The lamellar organization of the rat substantia nigra pars reticulata: distribution of projection neurons," Neuroscience, Jan. 1992, 46(2):361-377.

Dyr et al., "Effects of D1 and D2 dopamine receptor agents on ethanol consumption in the high-alcohol-drinking (HAD) line of rats," Alcohol, May/Jun. 1993, 10(3):207-212.

El-Ghundi et al., "Disruption of dopamine D1 receptor gene expression attenuates alcohol-seeking behavior," Eur. J. Pharmacology, Jul. 24, 1998, 353(2-3):149-158.

Everitt et al., "Drug Addiction: Updating Actions to Habits to Compulsions Ten Years On," Annu. Rev. Psychology, Aug. 7, 2015, 67:23-50.

Everitt et al., "From the ventral to the dorsal striatum: devolving views of their roles in drug addiction," Neurosci. Biobehav. Reviews, Nov. 2013, 37(9 Pt A):1946-1954.

Fanelli et al., "Dorsomedial and dorsolateral striatum exhibit distinct phasic neuronal activity during alcohol self-administration in rats," Eur. J. Neuroscience, Aug. 2013, 38(4):2637-2648.

Flora et al., "Deep Brain Stimulation for Essential Tremor: A Systematic Review," Mov. Disorders, Aug. 15, 2010, 25(11):1550-1559.

Follett, "The Surgical Treatment of Parkinson's Disease," Ann. Rev. Medicine, Feb. 2000, 51:135-147.

Gerfen et al., "Crossed connections of the substantia nigra in the rat," J. Comp. Neurology, May 20, 1982, 207(3):283-303.

Gerfen et al., "Modulation of Striatal Projection Systems by Dopamine," Annu. Rev. Neuroscience, 2011, 34:441-466.

Gradinaru et al., "Optical deconstruction of parkinsonian neural circuitry," Science, Apr. 17, 2009, 324(5925): 354-359.

Grado et al., "Effects of spike-time dependent plasticity on deep brain stimulation of the basal ganglia for treatment of Parkinson's disease," BMC Neuroscience, Dec. 2015, 16(Suppl. 1):P83.

Grill, "Temporal Pattern of Electrical Stimulation is a New Dimension of Therapeutic Innovation," Curr. Opin. Biomed. Engineering, Sep. 5, 2018, 8:1-6.

Halpern et al., "Deep brain stimulation in the treatment of obesity," J. Neurosurgery, Oct. 2008, 109(4):625-634.

Hearing et al., "Reversal of morphine-induced cell-type-specific synaptic plasticity in the nucleus accumbens shell blocks reinstatement," Proc. Natl. Acad. Sci. USA, Jan. 19, 2016, 113(3):757-762.

Heath et al., "Medium- and high-intensity rTMS reduces psychomotor agitation with distinct neurobiologic mechanisms," Transl. Psychiatry, Jul. 5, 2018, 8:126, 13 pages.

Heinze et al., "Counteracting incentive sensitization in severe alcohol dependence using deep brain stimulation of the nucleus accumbens: clinical and basic science aspects," Front. Hum. Neuroscience, Sep. 2, 2009, 3:22, 11 pages.

Hong et al., "Indirect Medium Spiny Neurons in the Dorsomedial Striatum Regulate Ethanol-Containing Conditioned Reward Seeking," J. Neuroscience, Sep. 4, 2019, 39(36):7206-7217.

Hwa et al., "Persistent Escalation of Alcohol Drinking in C57BL/6J Mice With Intermittent Access to 20% Ethanol," Alcohol. Clin. Exp. Research, Nov. 2011, 35(11):1938-1947.

Kimble et al., "Multifunctional System for Observing, Measuring and Analyzing Stimulation-Evoked Neurochemical Signaling," IEEE Int. Symp. Med. Meas. Applications, May 2017, 2017:349-354.

Knyazev, "Motivation, emotion, and their inhibitory control mirrored in brain oscillations," Neurosci. Biobehav. Reviews, 2007, 31(3):377-395.

(56) References Cited

OTHER PUBLICATIONS

Koob et al., "Neurobiology of addiction: a neurocircuitry analysis," Lancet Psychiatry, Aug. 2016, 3(8):760-773.
Koob et al., "Neurocircuitry of addiction," Neuropsychopharmacology, Aug. 26, 2009, 35(1):217-238.
Krauss, "Deep Brain Stimulation for Dystonia in Adults: Overview and Developments," Stereotact. Funct. Neurosurgery, 2002, 78(3-4):168-182.
Kuhn et al., "Remission of alcohol dependency following deep brain stimulation of the nucleus accumbens: valuable therapeutic implications?," J. Neurol. Neurosurg. Psychiatry, Oct. 2007, 78(10):1152-1153.
Lim et al., "Dopamine dysregulation syndrome, impulse control disorders and punding after deep brain stimulation surgery for Parkinson's disease," J. Clin. Neuroscience, Sep. 2009, 16(9):1148-1152.
Lima et al., "PINP: A New Method of Tagging Neuronal Populations for Identification during In Vivo Electrophysiological Recording," PLoS One, Jul. 7, 2009, 4(7):e6099, 10 pages.
Littel et al., "Changes in the electroencephalographic spectrum in response to smoking cues in smokers and ex-smokers," Neuropsychobiology, Mar. 6, 2009, 59(1):43-50.
London et al., "Coordinated Ramping of Dorsal Striatal Pathways preceding Food Approach and Consumption," J. Neuroscience, Apr. 4, 2018, 38(14):3547-3558 (2018).
Luigjes et al., "Deep brain stimulation in addiction: a review of potential brain targets," Mol. Psychiatry, Sep. 20, 2011, 17(6):572-583.
Lüscher et al., "Optogenetically inspired deep brain stimulation: linking basic with clinical research," Swiss Med. Weekly, Apr. 5, 2016, 146:w14278, 6 pages.
Ma et al., "Bidirectional and long-lasting control of alcohol-seeking behavior by corticostriatal LTP and LTD," Nat. Neuroscience, Feb. 12, 2018, 21(3):373-383.
McBride et al., "Densities of dopamine D2 receptors are reduced in CNS regions of alcohol-preferring P rats," Alcohol, Sep./Oct. 1993, 10(5):387-390.
McIntyre et al., "Excitation of Central Nervous System Neurons by Nonuniform Electric Fields, " Biophys. Journal, Feb. 1999, 76(2):878-888.
Müller et al., "Successful treatment of chronic resistant alcoholism by deep brain stimulation of nucleus accumbens: first experience with three cases," Pharmacopsychiatry, Nov. 2009, 42(6):288-291.
Nicolai et al., "Design Choices for Next-Generation Neurotechnology Can Impact Motion Artifact in Electrophysiological and Fast-Scan Cyclic Voltammetry Measurements," Micromachines, Sep. 27, 2018, 9(10):494, 18 pages.
Oh et al., "A mesoscale connectome of the mouse brain," Nature, Apr. 2, 2014, 508(7495):207-214.
Pelloux et al., "Deep brain stimulation for addiction: why the subthalamic nucleus should be favored," Curr. Opin. Neurobiology, Aug. 2013, 23(4):713-720.
Pelloux et al., "Subthalamic nucleus high frequency stimulation prevents and reverses escalated cocaine use," Mol. Psychiatry, Jun. 7, 2018, 23:2266-2276.
Perrin et al., "Bridging the gap between striatal plasticity and learning," Curr. Opin. Neurobiology, Oct. 12, 2018, 54:104-112.
Phillips et al., "Alcohol preference and sensitivity are markedly reduced in mice lacking dopamine D 2 receptors," Nat. Neuroscience, Nov. 1998, 1(7):610-615.
Popovych et al., "Desynchronizing electrical and sensory coordinated reset neuromodulation," Front. Hum. Neuroscience, Mar. 20, 2012, 6:58, 14 pages.
Putman, "Resting state EEG delta-beta coherence in relation to anxiety, behavioral inhibition, and selective attentional processing of threatening stimuli, " Int. J. Psychophysiology, Apr. 2011, 80(1):63-68.
Reid et al., "Quantitative electroencephalographic studies of cue-induced cocaine craving," Clin. Electroencephalogr., Jul. 2003, 34(3):110-123.
Robins et al., "Critical Role for Gi/o-Protein Activity in the Dorsal Striatum in the Reduction of Voluntary Alcohol Intake in C57Bl/6 Mice," Front. Psychiatry, Apr. 5, 2018, 9:112, 14 pages.
Roltsch Hellard et al., "Optogenetic control of alcohol-seeking behavior via the dorsomedial striatal circuit," Neuropharmacology, Sep. 2019, 155:89-97.
Sacks et al., "2010 National and State Costs of Excessive Alcohol Consumption," Am. J. Prev. Medicine, Nov. 2015, 49(5):e73-e79.
Servello et al., "Deep brain stimulation in 18 patients with severe Gilles de la Tourette syndrome refractory to treatment: the surgery and stimulation," J. Neurol. Neurosurg. Psychiatry, Feb. 2008, 79(2):136-142.
Shen et al., "Dichotomous Dopaminergic Control of Striatal Synaptic Plasticity," Science, Aug. 8, 2008, 321(5890):848-851.
Singla et al., "Mechanisms for Synapse Specificity during Striatal Long-Term Depression," J. Neuroscience, May 9, 2007, 27(19):5260-5264.
Smeding et al., "Pathological gambling after bilateral subthalamic nucleus stimulation in Parkinson disease," J. Neurol. Neurosurg. Psychiatry, Jan. 8, 2007, 78(5):517-519.
Stefanini et al., "Alcohol-preferring rats have fewer dopamine D2 receptors in the limbic system," Alcohol Alcoholism, Mar. 1992, 27(2):127-130.
Sweis et al., "Altering gain of the infralimbic-to-accumbens shell circuit alters economically dissociable decision-making algorithms," Proc. Natl. Acad. Sci. USA, Jul. 3, 2018, 115(27):E6347-E6355.
Swift et al., "Pharmacotherapy for Alcohol Use Disorder: Current and Emerging Therapies," Harv. Rev. Psychiatry, Mar./Apr. 2015, 23(2):122-133.
Thanos et al., "Overexpression of dopamine D2 receptors reduces alcohol self-administration," J. Neurochemistry, Sep. 2001, 78(5):1094-1103.
The Deep-Brain Stimulation for Parkinson's Disease Study Group, "Deep-Brain Stimulation of the Subthalamic Nucleus or the Pars Interna of the Globus Pallidus in Parkinson's Disease," N. Engl. J. Medicine, Sep. 27, 2001, 345(13):956-963.
Thomas et al., "Modulation of long-term depression by dopamine in the mesolimbic system," J. Neuroscience, Aug. 1, 2000, 20(15):5581-5586.
Trevathan et al., "Calcium imaging in freely-moving mice during electrical stimulation of deep brain structures," bioRxiv, Nov. 2, 2018, 23 pages.
Vignoud et al., "Interplay of multiple pathways and activity-dependent rules in STDP," PLoS Comput. Biology, Aug. 14, 2018, 14(8):e1006184, 32 pages.
Voges et al., "Deep Brain Stimulation Surgery for Alcohol Addiction," World Neurosurgery, Sep./Oct. 2013, 80(3-4):S28.e21-S28.e31.
Voigt et al., "Cathodic-leading pulses are more effective than anodic-leading pulses in intracortical microstimulation of the auditory cortex," J. Neural Engineering, Mar. 19, 2019, 16(2019):036002, 15 pages.
Volkow et al., "Decreases in dopamine receptors but not in dopamine transporters in alcoholics," Alcohol. Clin. Exp. Research, Dec. 1996, 20(9):1594-1598.
Wang et al., "Alcohol Elicits Functional and Structural Plasticity Selectively in Dopamine D1 Receptor-Expressing Neurons of the Dorsomedial Striatum," J. Neuroscience, Aug. 19, 2015, 35(33):11634-11643.
Wu et al., "Closing the loop on impulsivity via nucleus accumbens delta-band activity in mice and man," Proc. Natl. Acad. Sci. USA, Jan. 2, 2018, 115(1):192-197.
Wu et al., "Neurostimulation for the treatment of epilepsy: a review of current surgical interventions," Neuromodulation, Jan./Feb. 2013, 16(1):10-24.
Yin et al., "Ethanol reverses the direction of long-term synaptic plasticity in the dorsomedial striatum," Eur. J. Neuroscience, Jun. 2007, 25(11):3226-3232.

* cited by examiner

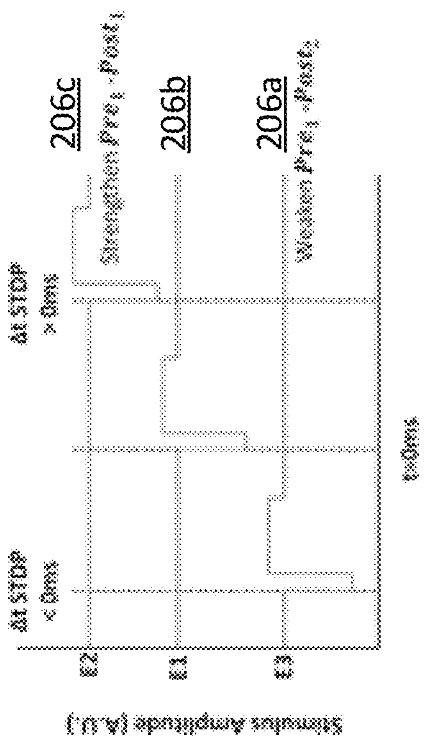
FIG. 2D
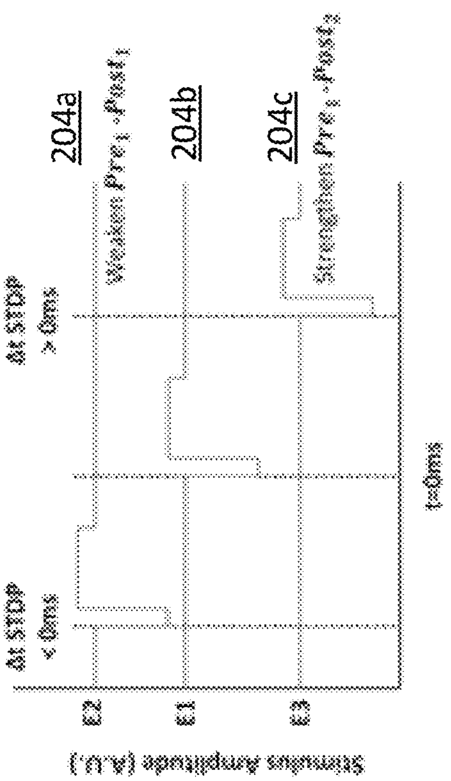
FIG. 2C

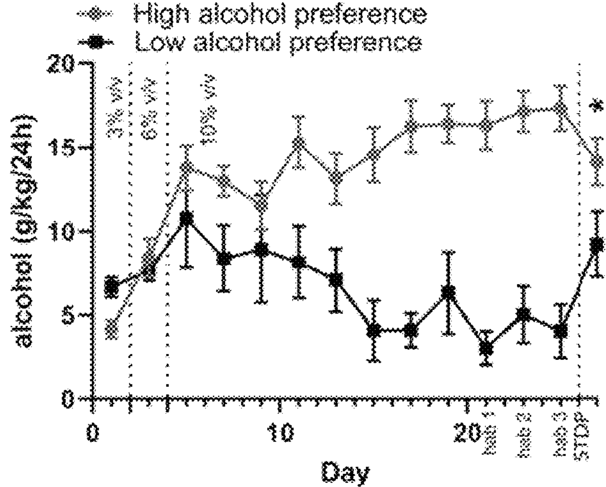
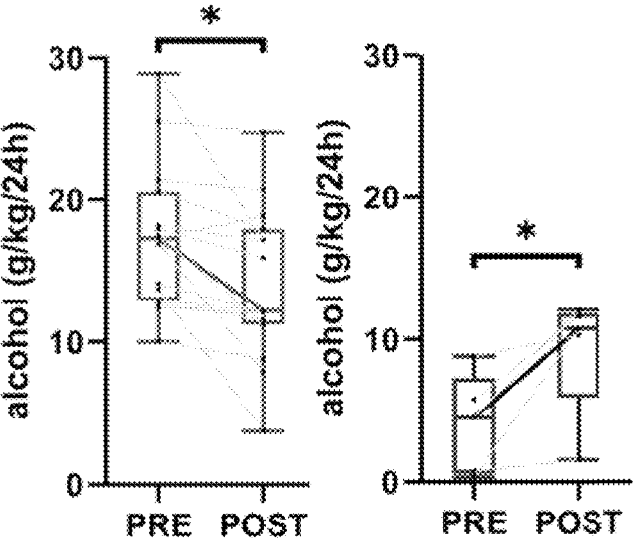
FIG. 8

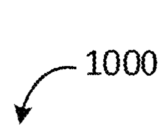

Apply a first electromagnetic pulse to a first neural element of a first neuron of the subject using a first electrode, where the first neural element includes a first synapse coupled to a second neuron of the subject
1002

Subsequent to applying the first electromagnetic pulse to the first neural element , apply a second electromagnetic pulse to a second neural element of the second neuron using a second electrode
1004

FIG. 10A

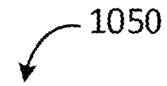

Apply a first electromagnetic pulse to a first neural element of a first neuron of the subject using a first electrode, where the first neural element includes a first synapse coupled to a second neuron of the subject
1052

Subsequent to applying the first electromagnetic pulse to the first neural element , apply a second electromagnetic pulse to a second neural element of a third neuron using a second electrode, where the second neural element includes a second synapse coupled to the first neuron
1054

FIG. 10B

BIDIRECTIONAL SPIKE-TIMING-DEPENDENT BRAIN NETWORK GAIN CONTROL

CROSS-REFERENCE TO RELATED APPLICATIONS

This application is a divisional of U.S. Utility application Ser. No. 17/394,366, filed Aug. 4, 2021, which claims the benefit of U.S. Patent Application Ser. No. 63/067,134, filed on Aug. 18, 2020. The disclosures of the prior applications are considered part of (and are incorporated by reference in) the disclosure of this application.

STATEMENT AS TO FEDERALLY SPONSORED RESEARCH

This invention was made with government support under NS107336 awarded by National Institutes of Health. The government has certain rights in the invention.

TECHNICAL FIELD

This disclosure relates to controlling synaptic gain, for example, in deep brain structures of a subject (e.g., a human or other mammal, animal, or individual).

BACKGROUND

Neuromodulation encompasses various techniques for modifying pathological activity within the nervous system (e.g., using electrical, electromagnetic, chemical, and/or optogenetic mechanisms) to achieve a therapeutic effect. Example neuromodulation techniques include deep brain stimulation (DBS), intracranial cortical stimulation (ICS), transcranial direct current stimulation (tDCS), and transcranial magnetic stimulation (TMS).

SUMMARY

In an aspect, a method for increasing and decreasing synaptic gain in a region of a brain of a subject, includes applying, using a first electrode, a first electromagnetic pulse to a first neural element of a first neuron of the subject, where the first neural element comprises a first synapse chemically or electrically coupled to a second neuron of the subject; and subsequent to applying the first electromagnetic pulse to the first neural element, applying, using a second electrode, a second electromagnetic pulse to a second neural element of the second neuron.

Implementations of this aspect can include one or more of the following features.

In some implementations the first neural element can include at least a portion of a dendrite, a soma, or an axon of the first neuron. Further, the second neural element can include at least a portion of a dendrite, a soma, or an axon of the second neuron.

In some implementations, the method can further include repeating, according to one or more repetitions, (i) applying the first electromagnetic pulse to the first neural element and (ii) subsequent to applying the first electromagnetic pulse to the first neural element, applying the second electromagnetic pulse to the second neural element.

In some implementations, the first electromagnetic pulse cam be applied starting at a first time, the second electromagnetic pulse can be applied starting at a second time, and a time interval between the first time and the second time can be between 1 milliseconds and 100 milliseconds.

In some implementations, each of the first pulse and the second pulse can be monophasic.

In some implementations, each of the first pulse and the second pulse can be multiphasic.

In some implementations, each of the first pulse and the second pulse can include a first pulse phase and a second pulse phase.

In some implementations, an amplitude of the first pulse phase can be different from the amplitude of the second pulse phase.

In some implementations, a duration of the first pulse phase can be different from a duration of the second pulse phase.

In some implementations, the first neuron can be disposed in at least one of a cortical region of the brain of the subject, a subcortical region of the brain of the subject, a spinal cord of the subject, or a peripheral nerve of the subject.

In some implementations, a method of treating a neurological condition can include determining that a subject has a neurological condition, and responsive to determining that the subject has the neurological condition, performing one or more of the methods described herein.

In some implementations, the neurological condition can be at least one of substance use disorder, obsessive compulsive disorder, chronic pain, Parkinson's Disease, Huntington's Disease, essential tremor, Tourette's Syndrome, major depressive disorder, post-traumatic stress disorder, schizophrenia, dementia, Alzheimer's Disease, epilepsy, urinary incontinence, mechanical injury, or biological injury.

In another aspect, a method for decreasing synaptic gain in a region of a brain of a subject includes applying, using a first electrode, a first electromagnetic pulse to a first neural element of a first neuron of the subject, where the first neural element comprises a first synapse chemically or electrically coupled to a second neuron of the subject; and subsequent to applying the first electromagnetic pulse to the first neural element, applying, using a second electrode, a second electromagnetic pulse to a second neural element of a third neuron, wherein the second neural element comprises a second synapse chemically or electrically coupled to the first neuron.

Implementations of this aspect can include one or more of the following features.

In some implementations the first neural element can include at least a portion of a dendrite, a soma, or an axon of the first neuron. Further, the second neural element can include at least a portion of a dendrite, a soma, or an axon of the third neuron.

In some implementations, the method can further include repeating, according to one or more repetitions, (i) applying the first electromagnetic pulse to the first neural element and (ii) subsequent to applying the first electromagnetic pulse to the first neural element, applying the second electromagnetic pulse to the second neural element.

In some implementations, the first electromagnetic pulse cam be applied starting at a first time, the second electromagnetic pulse can be applied starting at a second time, and a time interval between the first time and the second time can be between 1 milliseconds and 100 milliseconds.

In some implementations, each of the first pulse and the second pulse can be monophasic.

In some implementations, each of the first pulse and the second pulse can be multiphasic.

In some implementations, each of the first pulse and the second pulse can include a first pulse phase and a second pulse phase.

In some implementations, an amplitude of the first pulse phase can be different from the amplitude of the second pulse phase.

In some implementations, a duration of the first pulse phase can be different from a duration of the second pulse phase.

In some implementations, the first neuron can be disposed in at least one of a cortical region of the brain of the subject, a subcortical region of the brain of the subject, a spinal cord of the subject, or a peripheral nerve of the subject.

In some implementations, a method of treating a neurological condition can include determining that a subject has a neurological condition, and responsive to determining that the subject has the neurological condition, performing one or more of the methods described herein.

In some implementations, the neurological condition can be at least one of substance use disorder, obsessive compulsive disorder, chronic pain, Parkinson's Disease, Huntington's Disease, essential tremor, Tourette's Syndrome, major depressive disorder, post-traumatic stress disorder, schizophrenia, dementia, Alzheimer's Disease, epilepsy, urinary incontinence, mechanical injury, or biological injury.

The details of one or more embodiments are set forth in the accompanying drawings and the description below. Other features and advantages will be apparent from the description and drawings, and from the claims.

DESCRIPTION OF DRAWINGS

FIGS. 2A-2D show example sequences of electromagnetic pulses that can be applied to a subject using the system shown in FIG. 1.

FIGS. 5-9B show example data obtained from experimental studies that were conducted to develop pulse sequences for use in neuromodulation procedures.

FIG. 10A is a flow chart diagram of an example process for increasing synaptic gain in a region of a brain of a subject.

FIG. 10B is a flow chart diagram of an example process for decreasing synaptic gain in a region of a brain of a subject.

Like reference symbols in the various drawings indicate like elements.

DETAILED DESCRIPTION

Figure 1:
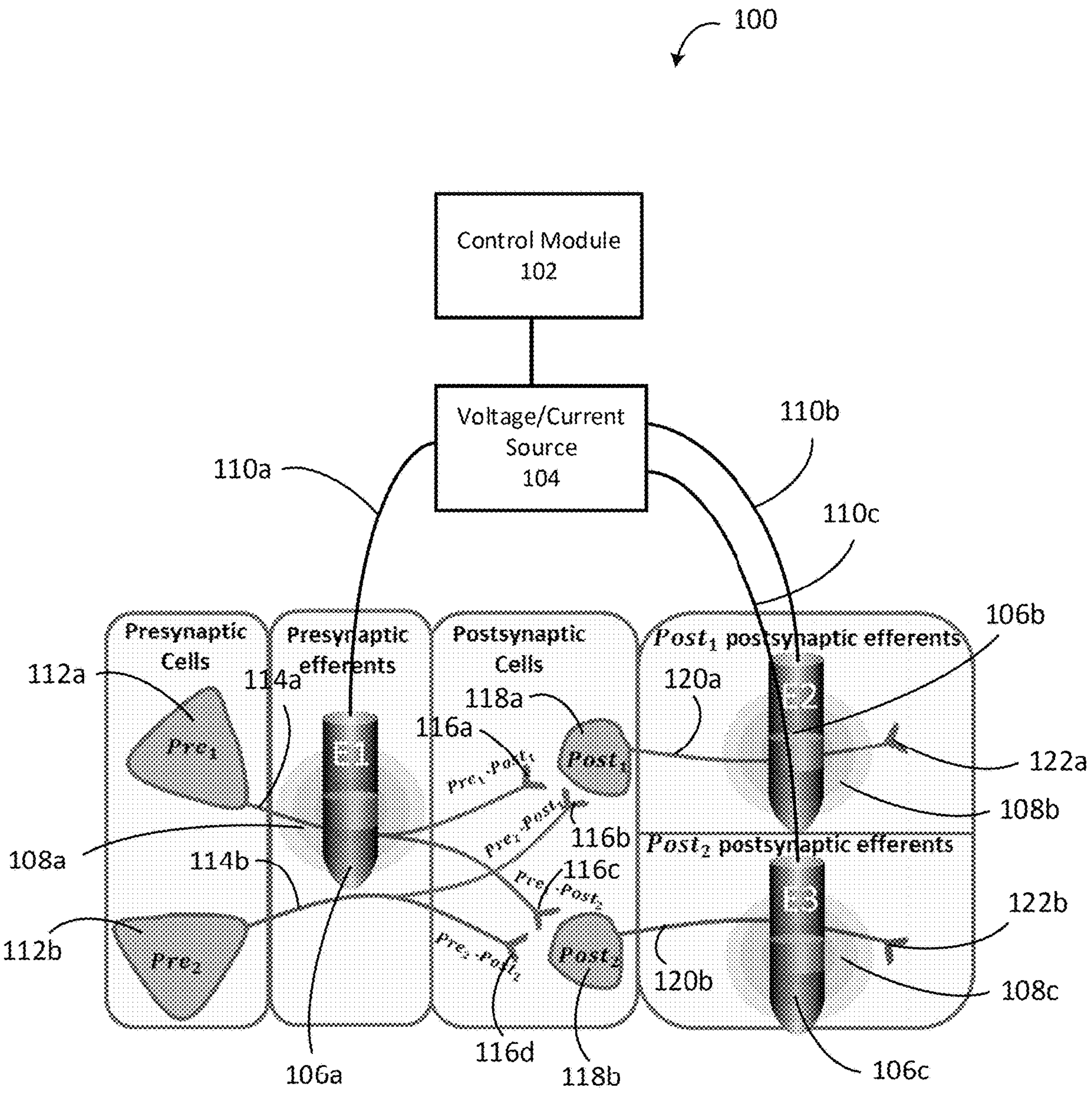
FIG. 1 is a diagram of system for performing a neuromodulation procedure.

An example system 100 for performing a neuromodulation procedure is shown in FIG. 1. The system 100 includes a control module 102, a voltage/current source 104, and several electrodes 106*a*-106*c* in electrical communication with the voltage/current source 104.

In an example use of the system 100, the electrodes 106*a*-106*c* are implanted into respective locations in a subject (e.g., such that they are in electrical communication with respective nerve fibers in the subject's brain). Further, the control module 102 instructs the voltage/current source 104 to generate one or more electromagnetic pulses and to deliver those electromagnetic pulses to respective ones of the electrodes 106*a*-106*c*, such that respective time-dependent electromagnetic fields 108*a*-108*c* are induced in the subject's body. These electromagnetic fields 108*a*-108*c*, for example, can influence the functionality of the subject's brain (e.g., to treat, alter, or otherwise mitigate neurological conditions suffered by the subject).

Each of the electrodes 106*a*-106*c* is configured to deliver electromagnetic pulses generated by the voltage/current source 104 (e.g., a voltage source, a current source, or both a voltage and current source) to specific locations in the subject's body. In some implementations, each of the electrodes 106*a*-106*c* can be composed, at least in part, of stainless steel, platinum, iridium, or any combination thereof. Each of the electrodes 106*a*-106*c* can be coupled (e.g., electrically coupled) to the voltage/current source 104 via a respective electrical conductor 110*a*-110*c* (e.g., an electrically conductive wire or cable). In some implementations, one, some, or all of the electrodes 106*a*-106*c* can have a monopole or multipolar electrode configuration. In some implementations, one, some, or all of the electrodes 106*a*-106*c* have a concentric ring contact configuration. In some implementations, one, some, or all of the electrodes 106*a*-106*c* have an arbitrary contact configuration on a single or multiple-shank electrode, including linear or multidimensional electrode arrays with or without current steering capabilities. In some implementations, one, some, or all of the electrodes 106*a*-106*c* can be invasive, minimally invasive, or noninvasive electrodes.

In some implementations, the system 100 can be used to deliver electromagnetic pulses to two or more locations of the subject's brain in succession. In some implementations, at least some of the electromagnetic pulses can be identical (or substantially identical) to one another. In some implementations, at least some of the electromagnetic pulses can be different from one another. In some implementations, a specific pulse sequence can be used to deliver multiple repetitions of an electromagnetic field to presynaptic neural elements for a defined interval (e.g., between 0-5 seconds, 0-10 seconds) prior to the delivery of a similar complementary electromagnetic field to neural elements of a postsynaptic cell. For example, the electromagnetic field can have an amplitude between 0 mA to 10 mA, a voltage between 0 to 15V, a frequency between 0 Hz to 1000 Hz, and a duration between 0 and up to about 10 seconds. Further, a specific pulse sequence can be used to selectively strengthen or weaken a multi-neuron network by delivering the electromagnetic field to presynaptic axons prior to postsynaptic axons.

For example, referring to FIG. 1, a subject's brain may include a number of neurons 112*a* and 112*b*, each having a respective neural element 114*a* and 114*b*. A neural element can include one or more portions of a respective neuron. For example, a neural element can include at least a portion of a dendrite, a soma, and/or an axon of a respective neuron. As another example, a neural element can include at least a portion of an efferent nerve fiber. Each of the neurons can be disposed in a cortical region of the brain of the subject, a subcortical region of the brain of the subject, a spinal cord of the subject, and/or a peripheral nerve of the subject.

Each of the neural elements 114*a* and 114*b* can have one or more synapses at its terminus or termini (e.g., if the neural element branches). In this example, the neural element 114*a* includes synapses 116*a* and 116*c* in electrical communication with neurons 118*a* and 118*b*, respectively, and the neural element 114*b* includes synapses 116*b* and 116*d* in electrical communication with neurons 118*a* and 118*b*, respectively. In turn, each of the neurons 118*a* and 118*b* can also include a respective neural element (e.g., neural elements 120*a* and 120*b*, respectively), each terminating at a respective synapse (e.g., synapses 122*a* and 122*b*, respectively) that are in communication with further neurons. In some cases, the neurons 112*a* and 112*b* may be referred to as "presynaptic cells," the neural elements 114*a* and 114*b* may be referred to as "presynaptic efferents," the neurons 118*a* and 118*b* may be referred to as "postsynaptic cells," and the neural elements 120*a* and 120*b* may be referred to as "postsynaptic efferents."

As shown in FIG. 1, a first electrode 106*a* can be positioned on or near the neural element 114*a* of the neuron 112*a* (extending to the neuron 118*a*), and a second electrode 106*b* can be positioned on or near the neural element 120*a* of the neuron 118*a* (extending to another neuron of the subject's brain). Further, electromagnetic pulses can be applied via control module 102 and voltage/current source 104 to the electrodes 106*a* and 106*b* in succession.

Figure 2B:
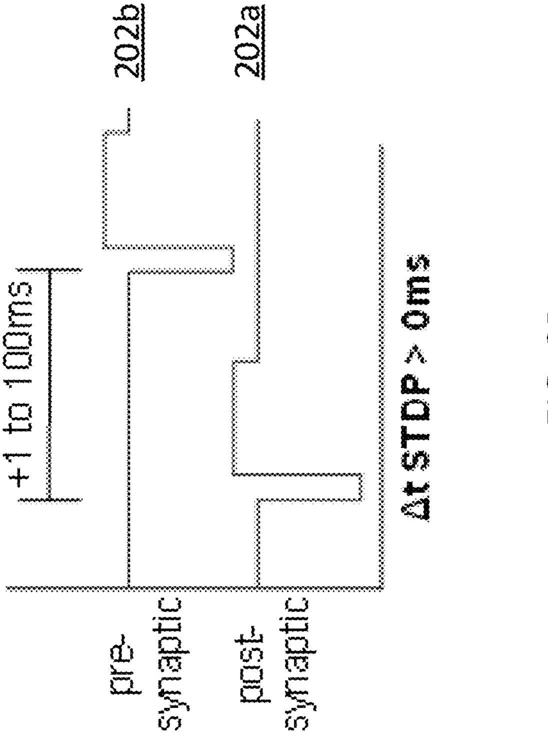
Figure 2A:
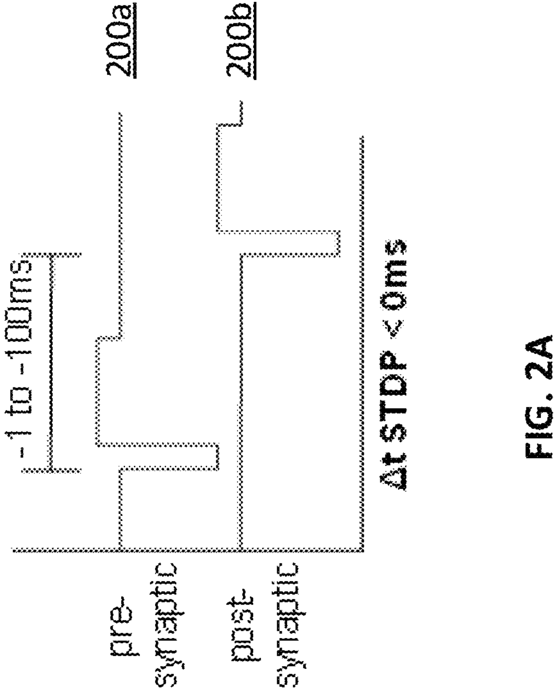

For example, as shown in FIG. 2A, a first electromagnetic pulse 200*a* can be applied to the electrode 106*a*. Further, after an interval of time, a second electromagnetic pulse 200*b* can be applied to the electrode 106*b*. In this manner, the synaptic gain in particular regions of the subject's brain (e.g., along the chain from the synapse 116*a*, the neuron 118*a*, the neural element 120*a*, and beyond) can be selectively increased.

In some implementations, stimulating the first "presynaptic" neural element prior to the second "postsynaptic" element can increase synaptic gain. In some implementations, stimulating the first "presynaptic" neural element prior to the second "postsynaptic" element can decrease in synaptic gain.

In some implementations, stimulating the first "presynaptic" neural element after the second "postsynaptic" element can increase synaptic gain. In some implementations, stimulating the first "presynaptic" neural element after the second "postsynaptic" element can decrease in synaptic gain.

In some implementations, synaptic gain may refer to the strength of the connection between two or more neurons. Synaptic gain can also be represented as coherence, synchrony, or information flow between brain regions. In some implementations, synaptic gain can be measured using electrophysiological analysis of extracellular spike frequency, miniature postsynaptic current frequency and amplitude, N-methyl-D-aspartate/N-Methyl-d-aspartic acid (AMPA/NMDA) ratio, motor-evoked potential, or evoked field postsynaptic potentials. In some implementations, synaptic gain can refer to molecular and histological neuronal characteristics including but not limited to expression of CamKII, brain-derived neurotrophic factor (BDNF), Calcienurin, cFos, Fosb, Arc, Egr2, Egr4, spine or neuronal morphology. Metabolic and functional markers of synaptic gain may include single-photon emission computed tomography (SPECT), positron emission tomography (PET), functional magnetic resonance imaging (fMRI), functional ultrasound, and tractographical analysis, among others.

In some implementations, the time interval between the beginning of the first electromagnetic pulse 200*a* and the second electromagnetic pulse 200*b* can be between about 1 millisecond to about 100 milliseconds. In some implementations, the time interval between the beginning of the first electromagnetic pulse 200*a* and the second electromagnetic pulse 200*b* can be greater than 0 seconds and less than or equal to about 10 seconds.

In some implementations, the time interval between the beginning of the first electromagnetic pulse 200*b* and the second electromagnetic pulse 200*a* can be between 1 millisecond and 100 milliseconds. In some implementations, the time interval between the beginning of the first electromagnetic pulse 200*b* and the second electromagnetic pulse 200*a* can be greater than 0 seconds and less than or equal to about 10 seconds.

For another example, as shown in FIG. 2B, a first electromagnetic pulse 202*a* can be applied to the electrode 106*b*. Further, after an interval of time, a second electromagnetic pulse 202*b* can be applied to the electrode 106*a*. This can be beneficial, for example, for selectively decreasing the synaptic gain in particular regions of the subject's brain (e.g., along the chain from the synapse 116*a*, the neuron 118*a*, the neural element 120*a*, and beyond) while not causing changes in synaptic gain in particular regions of the subject's brain (e.g., along the chain from synapse 116*c*, the neuron 118*b*, the neural element 120*b*, and beyond). In some implementations, the time interval between the beginning of the first electromagnetic pulse 202*a* and the second electromagnetic pulse 202*b* can be between about 1 millisecond to about 100 milliseconds. In some implementations, the time interval between the beginning of the first electromagnetic pulse 202*a* and the second electromagnetic pulse 202*b* can be greater than 0 seconds and less than or equal to 10 seconds.

Further, shown in FIG. 1, a third electrode 106*c* can be positioned on or near the neural element 120*c* of the neuron 118*a* (extending to another neuron of the subject's brain). Electromagnetic pulses can be applied to the electrodes 106*a*-106*c* in succession.

For example, as shown in FIG. 2C, a first electromagnetic pulse 204*a* can be applied to the electrode 106*b*. Further, after an interval of time, a second electromagnetic pulse 204*b* can be applied to the electrode 106*a*. Further, after another interval of time, a third electromagnetic pulse 204*c* can be applied to the electrode 106*c*. This can be beneficial, for example, for selectively decreasing the synaptic gain in particular regions of the subject's brain (e.g., along the chain from the synapse 116*a*, the neuron 118*a*, the neural element 120*a*, and beyond), while selectively increasing the synaptic gain in other regions of the subject's brain (e.g., along the chain from the synapse 116*c*, the neuron 118*b*, the neural element 120*b*, and beyond). In some implementations, the time interval between the beginnings of successive electromagnetic pulses can be between about 1 millisecond to about 100 milliseconds. In some implementations, the time interval between the beginnings of successive electromagnetic pulses can be greater than 0 seconds and less than or equal to about 10 seconds.

As another example, as shown in FIG. 2D, a first electromagnetic pulse 206*a* can be applied to the electrode 106*c*. Further, after an interval of time, a second electromagnetic pulse 206*b* can be applied to the electrode 106*a*. Further, after another interval of time, a third electromagnetic pulse 206*c* can be applied to the electrode 106*b*. This can be beneficial, for example, for selectively decreasing the synaptic gain in particular regions of the subject's brain (e.g., along the chain from the synapse 116*c*, the neuron 118*b*, the neural element 120*b*, and beyond), while selectively increasing the synaptic gain in other regions of the subject's brain (e.g., along the chain from the synapse 116*a*, the neuron 118*a*, the neural element 120*a*, and beyond). In some implementations, the time interval between the beginnings of successive electromagnetic pulses can be between 1 millisecond to 100 milliseconds. In some implementations, the time interval between the beginnings of successive electromagnetic pulses can be greater than 0 seconds and less than or equal to about 10 seconds.

Although three example electrodes are shown in FIG. 1, in practice, any number of electrodes two or greater can be used in any number of brain locations (e.g., two, three, four, etc.). Further, although example sequences of electromagnetic pulses are shown in FIGS. 2A-2D, in practice, other sequences of electromagnetic pulses also can be used.

In some implementations, at least some of the electromagnetic pulses can be identical or substantially identical to one another. In some implementations, at least some of the electromagnetic pulses can be different from one another.

In some implementations, each of the electromagnetic pulses can be charge balanced or charge imbalanced.

In some implementations, each of the electromagnetic pulses can be monophasic or multiphasic.

In some implementations, each of the electromagnetic pulses can include one or more square-shaped sub-pulses or one or more arbitrarily-shaped sub-pulses (e.g., curved, exponential, etc.).

In some implementations, the onset of each of the electromagnetic pulses can be characterized by the full width half maximal point of the rising phase.

In some implementations, the timing between the activation of individual electrodes can be selected by taking into account the conduction velocity of action potential propagation, the nonlinearity of white matter pathways, and/or the position of the electrode with respective to three-dimensional neuroanatomical structures. The timing parameters can be set in control module 102 and stored in memory therein. In some implementations, timing parameters are preset in the control module 102. In some implementations, timing parameters are received by the control module 102 based on user input at the control module 102 or received wirelessly or view a wired connection to a separate device. In some implementations, the control module 102 sets/adjusts the timing parameters based on automatically detected conditions, e.g., conditions related to the conduction velocity of action potential propagation, the nonlinearity of white matter pathways, and/or the position of the electrode with respective to three-dimensional neuroanatomical structures.

The electrodes can be positioned in various locations in the subject's body. As an example, the electrodes can be positioned in cortical regions of the subject's brain, including, but not limited to, the anterior cingulate cortex, infralimbic cortex, prelimbic cortex, orbitofrontal cortex, prefrontal cortex, subgenual cingulate cortex (CG25), subcallosal cingulate cortex, motor cortex (M1), supplemental motor cortex, somatosensory cortex, insular cortex, all white matter bundles, anterior commissure, inferior parietal lobe, temporal lobe, and corpus callosum As an example, the electrodes can be positioned in subcortical regions of the subject's brain, including, but not limited to, the globus pallidus internal segment, globus pallidus external segment, thalamus, hypothalamus, thalamic peduncle, subthalamic nucleus, hippocampus, striatum, caudate, putamen, nucleus accumbens core and shell, ventral pallidum, cerebellum, red nucleus, pontine nucles, brainstem nuclei, periaqueductal grey, post and pre central gyri, substantia nigra, habenula, amygdala, spinal cord, locus coeruleus, raphe nuclei, reticular formation, all white matter bundles, ventral capsule, medial forebrain bundle, and hyperdirect pathway As an example, the electrodes can be positioned in the subject's peripheral nerves, including, but not limited to the spinal nerves, brachial plexus, cervical plexus, sacral plexus, coccygeal nerves, thoracoabdominal nerves, lumbrosacral plexus, splanchnic nerve, craniofacial nerves, vagus nerve, and phrenic nerve.

Further, in some implementations, one or more neural elements can be simulated mechanically, via ephaptic coupling, and/or using an electromagnetic pulse, either instead of or in addition to the electrode-based techniques described above.

The systems and techniques described herein can provide various technical benefits. As an example, at least some of the systems and techniques described herein allows for neural network-level gain control in deep brain structures. For instance, by delivering an electromagnetic field to at least two spatially unique neural elements in a temporally sequenced manner, synaptic gain in a third region can be increased or decreased. In some implementations, this approach emulates a natural phenomenon underlying learning and memory known as spike timing dependent plasticity (STDP).

Further, in some implementations, the systems and techniques describes herein can be used to treat or otherwise mitigate neurological conditions suffered by the subject. For example, at least some of the systems and techniques described herein can be used to deliver targeted STDP for reversing pathway-specific maladaptive synaptic gain observed in neurological conditions including, but not limited to depression, post-traumatic stress disorder (PTSD), attention deficit hyperactivity disorder (ADHD), addiction, substance use disorder, Parkinson's disease (both psychiatric and motor aspects), chronic pain, Huntington's Disease, essential tremor, Tourette's Syndrome, major depressive disorder, post-traumatic stress disorder, schizophrenia, dementia, Alzheimer's Disease, epilepsy, urinary incontinence, mechanical injury, or biological injury.

Further, least some of the systems and techniques described herein can be used in gain-of-function applications, such as to enhance memory, learning, cognition, and motor function (e.g., in otherwise healthy individuals).

Further, least some of the systems and techniques described herein can facilitate precise control over neural connections contributing to neurological disease, while avoiding or otherwise reducing off-target disruption of non-pathological brain activity responsible for causing undesirable side-effects. Further, least some of the systems and techniques described herein can enable for the treatment of intractable psychiatric conditions for which there may be no known cures.

Example Experimental Data

Example experimental studies were conducted to develop pulse sequences for use in neuromodulation procedures.

Figure 3:
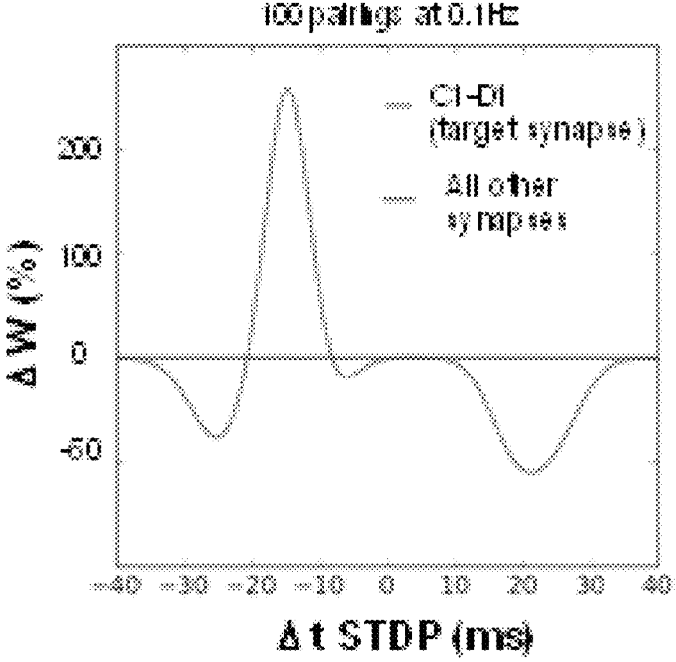
FIG. 3 depicts an example mathematical model suggesting that an optimal (or other beneficial) synapse strengthening and weakening can be achieved at Δt STDP of −19 ms and +21 ms.

First, as shown in FIG. 3, a mathematical model was generated, which suggests that an optimal (or other beneficial) synapse strengthening and weakening can be achieved at Δt STDP of −19 ms and +21 ms, respectively. These results provide computation evidence that temporal differences in pre- and post-synaptic action potentials alters synaptic strength, weight, or gain. FIG. 3 is adapted from Cui, Y. et al. Endocannabinoid dynamics gate spike-timing dependent depression and potentiation. e Life 5, e13185

Figure 4:
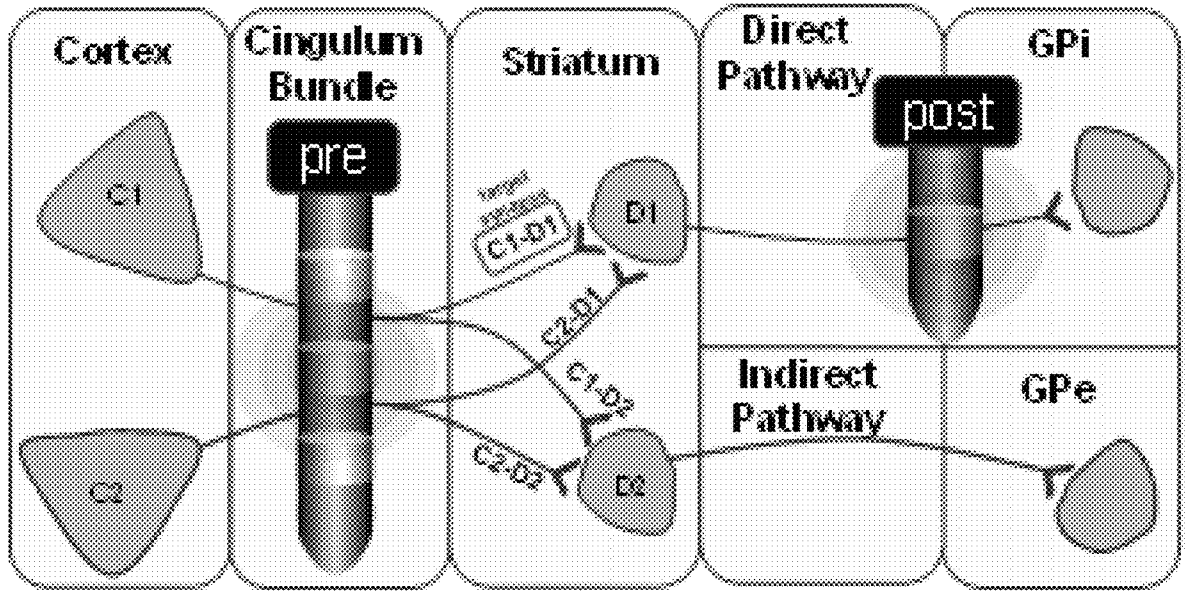
FIG. 4 shows a simplified example of a two-neuron network of the corticostriatal synapse.

(2016). Referring to FIG. 4, an electrical stimulus was applied to both cortical axons C1 and C2 within a (+/−100 ms) temporal window of stimulating postsynaptic axons D1.

Further, as described above, a benefit of the techniques described herein includes an ability to exert targeted control over specific elements of a brain network while avoiding off-target influence on brain function and network connectivity. For instance, an example of a two-neuron network is the corticostriatal synapse, a simplified representation of which is shown in FIG. 4. In this simple circuit, multiple cortical axons project to multiple subtypes of striatal cells including striatal projection neurons (SPNs) which project to either the direct pathway or indirect pathway. When the previously described low frequency, low duty-cycle stimulation sequence is applied to either the presynaptic axons or the postsynaptic axons alone, no change in network gain is observed. However, selective bidirectional gain control of the synapse between cortical cell C1 and direct pathway cell D1 can be achieved by repeatedly delivering a timed stimulation sequence to the presynaptic axons in the cingulum bundle and the postsynaptic SPN axons projecting to the internal globus pallidus (GPi) while avoiding activation of SPNs which project to the GPe.

Figure 5:
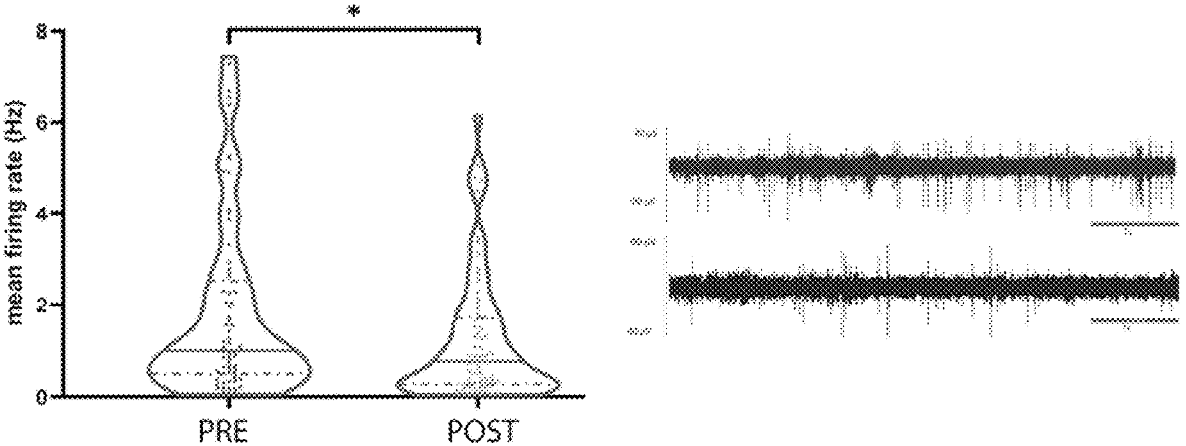

As shown in FIG. 5, spike-timing-dependent stimulation of the pathway described with reference to FIG. 1 with protocol described with reference to FIG. 2B decreases the mean firing rate of medium spiny neuron units in the dorsal medial striatum. n=96 units, 3 awake unrestrained mice (left). Example traces as shown from the striatum before (top right) and after (bottom right) application of spike-timing-dependent plasticity inducing the protocol described with reference to FIG. 2B.

Figure 6:
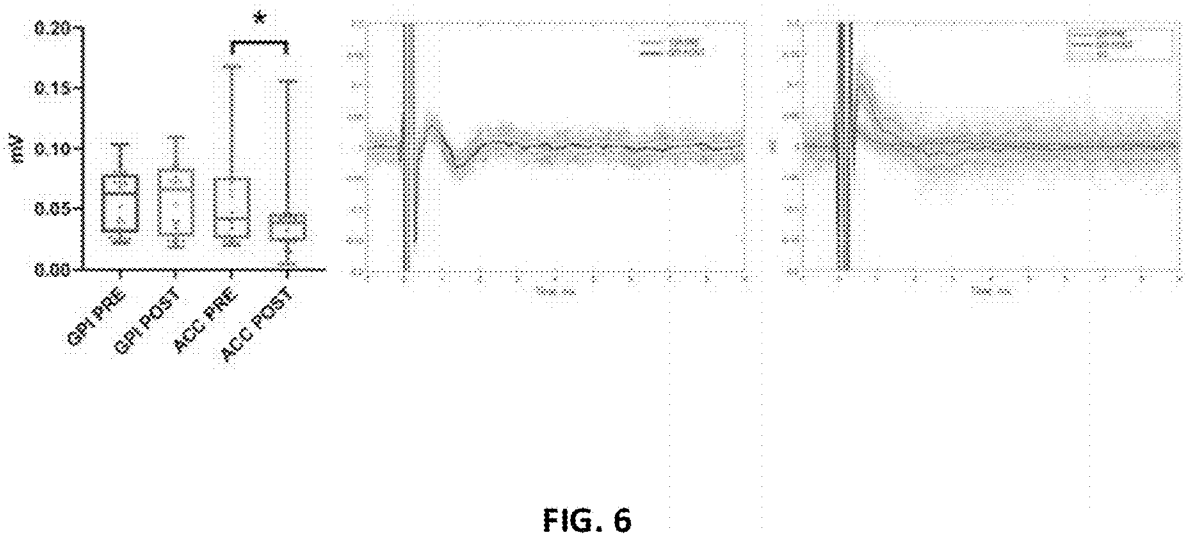

FIG. 6 shows the compound action potential in striatum evoked by GPi and ACC stimulation before (PRE) and after (POST) stimulation of pathway described with reference to FIG. 1 with the protocol described with reference to FIG. 2B (left). This demonstrates representative amplitude and latencies of compound action potential in DMS evoked by GPi (middle) and ACC (right) stimulation. Box and whisker plots represent median, 95% CI, and max/minimum where back dots represent individual electrodes.

Figure 7:
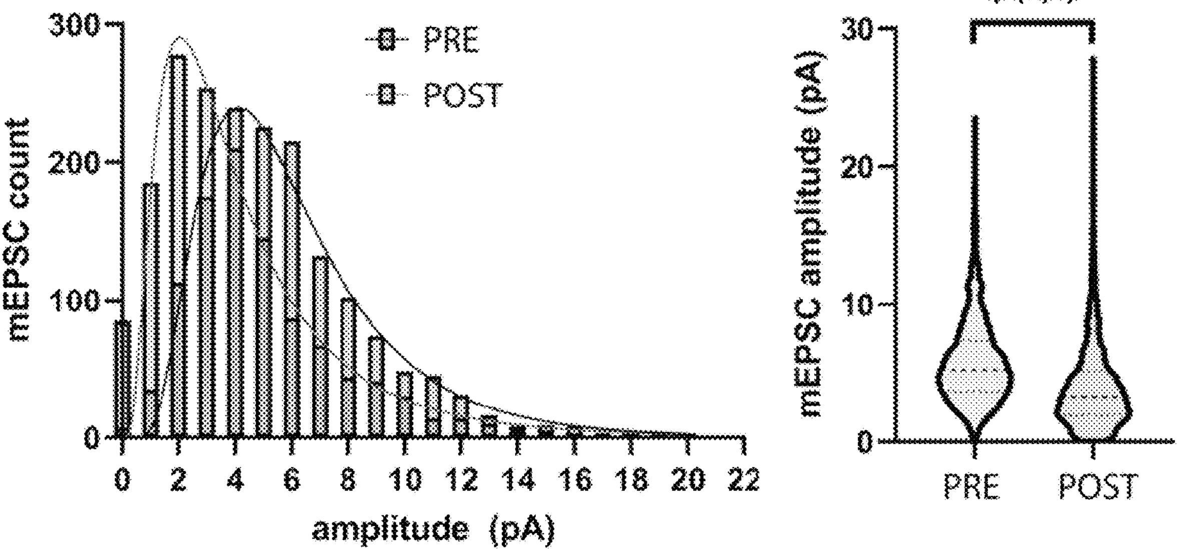

As shown in FIG. 7, spike-timing-dependent stimulation of the pathway described with reference to FIG. 1 with the protocol described with reference to FIG. 2B decreases amplitude of miniature excitatory postsynaptic currents (mEPSC) of medium spiny neuron units in the dorsal medial striatum measured ex vivo with whole cell patch clamp electrophysiology.

As shown in FIG. 8, studies were conducted to determine whether the spike-timing-dependent stimulation of the pathway described with reference to FIG. 1 with the protocol described with reference to FIG. 2B applied in vivo can reverse pathological synaptic gain underlying alcohol consumption in a two-bottle choice mouse model of alcohol use disorder. Chronic alcohol consumption leads to persistent hyperactivity of Dopamine receptor 1-containing medium spiny neurons (D1-MSNs) projecting to the GPi via the direct pathway and a persistent hypoactivity of Dopamine receptor 2-containing medium spiny neurons (D2-MSNs) of the Dorsomedial Striatum (DMS) projecting to the GPe via the indirect pathway. Reducing this imbalance using optogenetics or chemogenetics decreases alcohol seeking behavior. In mice exhibiting alcohol preference >60% and direct pathway hyperactivity, we applied our positive STDP protocol designed to decrease synaptic gain (e.g., as shown in FIG. 2A) to the cingulum bundle and GPi, which reduced alcohol consumption (FIG. 8 red). Conversely, in mice exhibiting alcohol preference <60%, the negative STDP protocol was applied to increase synaptic gain (e.g., as shown in FIG. 2B) to the cingulum bundle and GPi, which increased alcohol consumption (FIG. 8 black).

As shown in FIG. 8, spike timing-dependent stimulation of the ACC and GPi using the approach described with reference to FIG. 2B (red) and FIG. 2A (black) promotes bidirectional control of alcohol consumption in a two-bottle choice model of alcohol use disorder (top). In particular, FIG. 8 shows example results from a bidirectional control of alcohol consumption in a two-bottle choice experiment. Chronic EtOH exposure increases synaptic strength of the synapse between elements 116*a* and 118*a* indicated in FIG. 1. At day 26, high alcohol preference animals (>60%) were given a STDP (spike-timing dependent plasticity) protocol to induce long term depression (LTD) in the "C1-D1" corticostriatal synapse (n=6). The protocol included applying a charge balance cathodic leading, biphasic, 1 HZ 250 μA, 90 μs stimulation from electrode 106*a* for 10 minutes to element 114*a* which includes axons projecting from the anterior cingulate cortex (ACC) paired with stimulation of element 120*a* with electrode 106*b* in the internal globus pallidus (GPi) occurring 18 ms prior to ACC simulation ($\Delta t=+18$ ms). Similarity, low alcohol preference animals (<60%) were given a STDP protocol described in 2A to induce LTP in the 116*a* to 118*a* synapse (n=4) in which all simulation parameters were identical to the LTD protocol with the exception of delivery ACC stimulation 13 ms prior to GPi stimulation ($\Delta t=-13$ ms). Statistical significance was determined using a two-tailed paired t-test with $P<0.05$ A detailed view of the last two data points showing alcohol consumption in g/kg/24 hour is also shown (bottom). "PRE" indicates the 24 hours before stimulation and "POST" indicates the 24 hours after stimulation. Error bars represent SEM (top) while Box and whisker plots represent median, 95% CI, and max/minimum where back dots and gray lines represent individual animals.

Figure 9A:
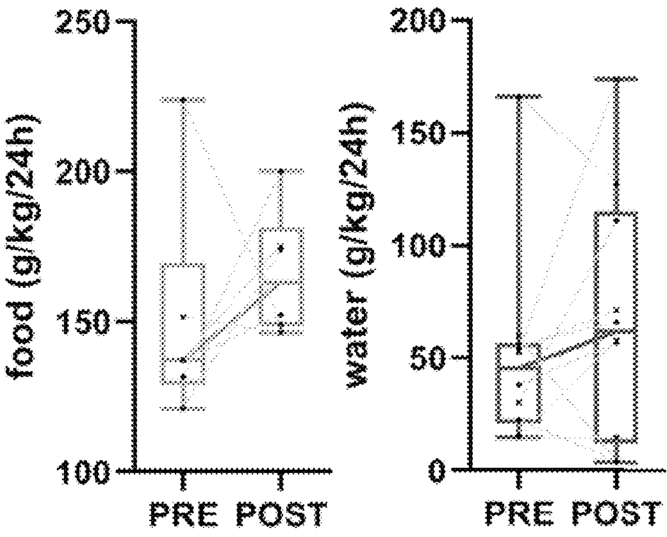

As shown in FIG. 9A, spike-timing-dependent stimulation of the ACC and GPi using the approach described with reference to FIG. 2B (red) decreases alcohol consumption in a two-bottle choice model of AUD without decreasing food or water consumption, indicating targeted control of maladaptive alcohol consumption behavior while avoiding side effects on other motivated behavior. Box and whisker plots represent median, 95% CI, and max/minimum where back dots and gray lines represent individual animals.

Figure 9B:
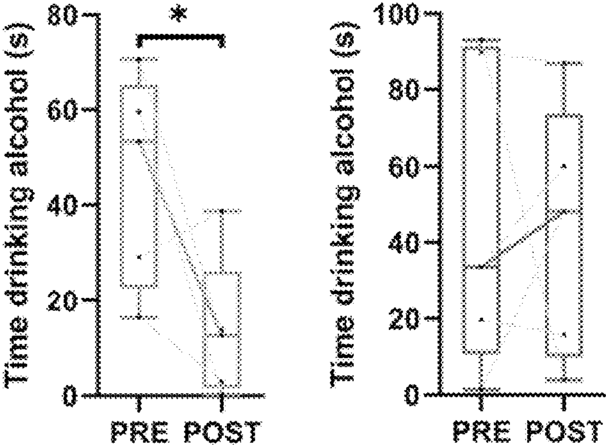

As shown in FIG. 9B, spike-timing-dependent stimulation of the ACC and GPi using the approach described with reference to FIG. 2B decreases alcohol consumption in a two-bottle choice model of AUD first 170 minutes of the night cycle (left), but this decrease is absent 360-490 after stimulation and thereafter.

These example results demonstrate the efficacy for this STDP neuromodulation approach and demonstrate that physiological engagement can be achieved both in vitro and in vivo. As an added benefit of this approach, low frequency and low duty cycle stimulation confers the advantage of lower power requirements, resulting in significant improvement in battery life if delivered through implantable pulse generators and obviating the need for surgical battery replacement (e.g., every four years on average), which comes with additional costs, risk of infection, and undue subject suffering.

Example Processes

An example process 1000 for increasing synaptic gain in a region of a brain of a subject is shown in FIG. 10A. In some implementations, the process 1000 can be performed, at least in part, using the system 100 shown in FIG. 1.

According the process 1000, a first electromagnetic pulse is applied to a first neural element of a first neuron of the subject using a first electrode (step 1002). The first neural element includes a first synapse coupled (e.g., electrically and/or chemically coupled) to a second neuron of the subject. As an example, referring to FIG. 1, a first electromagnetic pulse can be applied to the neural element 114*a* using the electrode 106*a*.

In some implementations, the first neural element can include at least a portion of a dendrite, a soma, an axon, and/or any other portion of the first neuron. Further, the second neural element can include at least a portion of a dendrite, a soma, an axon and/or any other portion of the second neuron.

Subsequent to applying the first electromagnetic pulse to the first neural element, a second electromagnetic pulse is applied to a second neural element of the second neuron using a second electrode (step 1004). As an example, referring to FIG. 1, a second electromagnetic pulse can be applied to the neural element 120*a* using the electrode 106*b*.

In some implementations, the application of the first and second electromagnetic pulses can be repeated one or more times in a sequence. For example, the following can be repeated according to one or more repetitions: (i) applying the first electromagnetic pulse to the first neural element and (ii) subsequent to applying the first electromagnetic pulse to the first neural element, applying the second electromagnetic pulse to the second neural element.

In some implementations, the first electromagnetic pulse can be applied starting at a first time, the second electromagnetic pulse can be applied starting at a second time, and a time interval between the first time and the second time can between 1 milliseconds and 100 milliseconds.

In some implementations, each of the first pulse and the second pulse can be monophasic.

In some implementations, each of the first pulse and the second pulse can be multiphasic.

In some implementations, each of the first pulse and the second pulse can include a first signal portion and a second signal portion in a sequence. An amplitude of the first signal portion can be different from an amplitude of the signal second portion. For example, the amplitude of the first signal portion can be less than or greater than the amplitude of the second signal portion. Further, a duration of the first signal portion can be different from a duration of the second signal portion. For example, a duration of the first signal portion can be less than or greater than a duration of the second signal portion.

In some implementations, each of the first pulses can be applied multiple times prior to application of the second pulse. Further, the second pulse also can be applied multiple times.

In some implementations, the process 1000 can be performed as a part of a procedure for treating a neurological condition. For example, a determination can be made that subject has a neurological condition, and in response, the process 1000 can be performed with respect to the subject.

In some implementations, the neurological condition can be at least one of substance use disorder, obsessive compulsive disorder, chronic pain, Parkinson's Disease, Huntington's Disease, essential tremor, Tourette's Syndrome, major depressive disorder, post-traumatic stress disorder, schizophrenia, dementia, Alzheimer's Disease, epilepsy, urinary incontinence, mechanical injury, or biological injury.

In some implementations, the first neural element and/or the second neural element can be stimulated mechanically.

In some implementations, the first neural element and/or the second neural element can be stimulated via ephaptic coupling.

In some implementations, the first neural element and/or the second neural element can be stimulated using an electromagnetic pulse.

An example process 1050 for decreasing synaptic gain in a region of a brain of a subject is shown in FIG. 10B. In some implementations, the process 1050 can be performed, at least in part, using the system 100 shown in FIG. 1.

According the process 1050, a first electromagnetic pulse is applied to a first neural element of a first neuron of the subject using a first electrode (step 1052). The first neural element includes a first synapse coupled (e.g., electrically and/or chemically coupled) to a second neuron of the subject. As an example, referring to FIG. 1, a first electromagnetic pulse can be applied to the neural element 120*a* using the electrode 106*b*.

Subsequent to applying the first electromagnetic pulse to the first neural element, a second electromagnetic pulse is applied to a second neural element of a third neuron using a second electrode (step 1054). The second neural element includes a second synapse coupled (e.g., electrically and/or chemically coupled) to the first neuron. As an example, referring to FIG. 1, a second electromagnetic pulse can be applied to the neural element 114*a* using the electrode 106*a*.

In some implementations, the first neural element can include at least a portion of a dendrite, a soma, an axon, and/or any other portion of the first neuron. Further, the second neural element can include at least a portion of a dendrite, a soma, an axon and/or any other portion of the third neuron.

In some implementations, the application of the first and second electromagnetic pulses can be repeated one or more times in a sequence. For example, the following can be repeated according to one or more repetitions: (i) applying the first electromagnetic pulse to the first neural element and (ii) subsequent to applying the first electromagnetic pulse to the first neural element, applying the second electromagnetic pulse to the second neural element.

In some implementations, the first electromagnetic pulse can be applied starting at a first time, the second electromagnetic pulse can be applied starting at a second time, and a time interval between the first time and the second time can be between 1 milliseconds and 100 milliseconds.

In some implementations, each of the first pulse and the second pulse can be monophasic.

In some implementations, each of the first pulse and the second pulse can be multiphasic.

In some implementations, each of the first pulse and the second pulse can include a first signal portion and a second signal portion in a sequence. An amplitude of the first signal portion can be different from an amplitude of the signal second portion. For example, the amplitude of the first signal portion can be less than or greater than the amplitude of the second signal portion. Further, a duration of the first signal portion can be different from a duration of the second signal portion. For example, a duration of the first signal portion can be less than or greater than a duration of the second signal portion.

In some implementations, the process 1050 can be performed as a part of a procedure for treating a neurological condition. For example, a determination can be made that subject has a neurological condition, and in response, the process 1050 can be performed with respect to the subject.

In some implementations, the neurological condition can be at least one of substance use disorder, obsessive compulsive disorder, chronic pain, Parkinson's Disease, Huntington's Disease, essential tremor, Tourette's Syndrome, major depressive disorder, post-traumatic stress disorder, schizophrenia, dementia, Alzheimer's Disease, epilepsy, urinary incontinence, mechanical injury, or biological injury.

Example Systems

Some implementations of subject matter and operations described in this specification can be implemented in digital electronic circuitry, or in computer software, firmware, or hardware, including the structures disclosed in this specification and their structural equivalents, or in combinations of one or more of them. For example, in some implementations, the control module 102 can be implemented using digital electronic circuitry, or in computer software, firmware, or hardware, or in combinations of one or more of them.

Some implementations described in this specification can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and optical disks (e.g., CD-ROM disks, DVD-ROM disks, Blu-ray disks, etc.). The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 11:
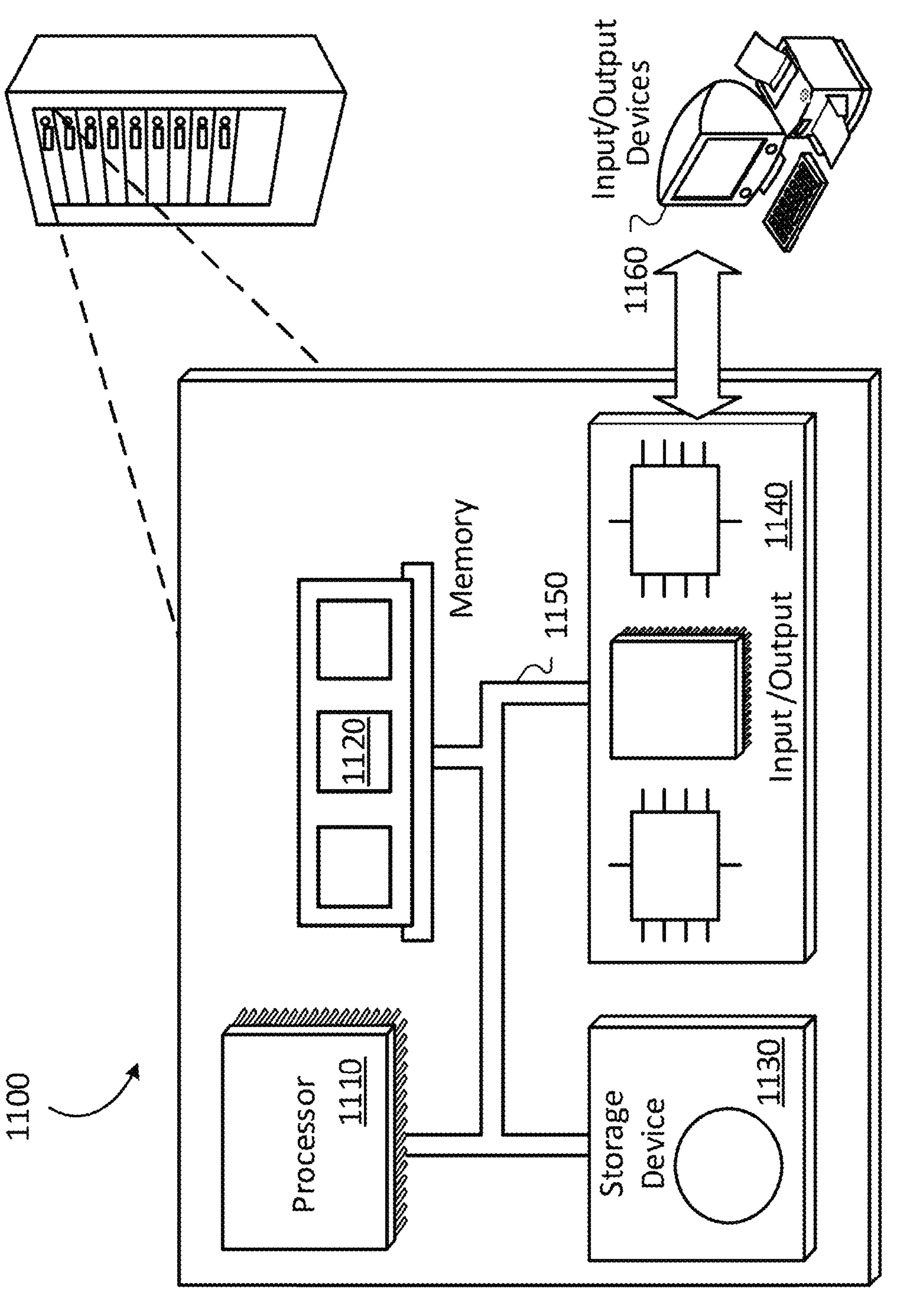
FIG. 11 is a diagram of an example computer system.

FIG. 11 shows an example computer system 1100 that includes a processor 1100, a memory 1120, a storage device 1130 and an input/output device 1140. Each of the components 1110, 1120, 1130 and 1140 can be interconnected, for example, by a system bus 1150. The processor 1110 is capable of processing instructions for execution within the system 1100. In some implementations, the processor 1110 is a single-threaded processor, a multi-threaded processor, or another type of processor. The processor 1110 is capable of processing instructions stored in the memory 1120 or on the storage device 1130. The memory 1120 and the storage device 1130 can store information within the system 1100.

The input/output device 1140 provides input/output operations for the system 1100. In some implementations, the input/output device 1140 can include one or more of a network interface device, e.g., an Ethernet card, a serial communication device, e.g., an RS-232 port, and/or a wireless interface device, e.g., an 802.11 card, a 3G wireless modem, a 4G wireless modem, a 5G wireless modem, etc. In some implementations, the input/output device can include driver devices configured to receive input data and send output data to other input/output devices, e.g., keyboard, printer and display devices 1160. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of implementations have been described. Nevertheless, it will be understood that various modifications may be made without departing from the spirit and scope of the invention. Accordingly, other implementations are within the scope of the following claims.

What is claimed is:

1. A method for increasing synaptic gain in a region of a brain of a subject, the method comprising:

applying, using a first electrode, a first electromagnetic pulse to a first neural element of a first neuron of the subject, wherein the first neural element comprises a first synapse coupled to a second neuron of the subject; and subsequent to applying the first electromagnetic pulse to the first neural element, applying, using a second electrode, a second electromagnetic pulse to a second neural element of the second neuron.

2. The method of claim 1, wherein the first neural element comprises at least a portion of a dendrite, a soma, or an axon of the first neuron, and wherein the second neural element comprises at least a portion of a dendrite, a soma, or an axon of the second neuron.

3. The method of claim 1, further comprising:

repeating, according to one or more repetitions, (i) applying the first electromagnetic pulse to the first neural element and (ii) subsequent to applying the first electromagnetic pulse to the first neural element, applying the second electromagnetic pulse to the second neural element.

4. The method of claim 1, wherein the first electromagnetic pulse is applied starting at a first time, wherein the second electromagnetic pulse is applied starting at a second time, and wherein a time interval between the first time and the second time is between 1 milliseconds and 100 milliseconds.

5. The method of claim 1, wherein each of the first pulse and the second pulse are monophasic.

6. The method of claim 1, wherein each of the first pulse and the second pulse are multiphasic.

7. The method of claim 1, wherein each of the first pulse and the second pulse comprises a first pulse phase and a second pulse phase, and wherein at least one of:

an amplitude of the first pulse phase is different from the amplitude of the second pulse phase a duration of the first pulse phase is different from a duration of the second pulse phase.

8. The method of claim 1, wherein the first neuron is disposed in at least one of a cortical region of the brain of the subject, a subcortical region of the brain of the subject, a spinal cord of the subject, or a peripheral nerve of the subject.

9. A method of treating a neurological condition, determining that a subject has a neurological condition, and responsive to determining that the subject has the neurological condition, performing the method of claim 1.

10. The method of claim 9, wherein the neurological condition is at least one of:

substance use disorder, obsessive compulsive disorder, chronic pain, Parkinson's Disease, Huntington's Disease, essential tremor, Tourette's Syndrome, major depressive disorder, post-traumatic stress disorder, schizophrenia, dementia, Alzheimer's Disease, epilepsy, urinary incontinence, mechanical injury, or biological injury.

11. The method of claim 1, wherein the first synapse is chemically coupled to the second neuron of the subject.

12. The method of claim 1, wherein the first synapse is electrically coupled to the second neuron of the subject.

13. The method of claim 1, wherein the first synapse is electrically coupled and chemically coupled to the second neuron of the subject.

* * * * *